United States Patent [19]
Ahmed

[11] Patent Number: 5,728,061
[45] Date of Patent: Mar. 17, 1998

[54] DEVICE AND METHOD FOR TREATING HYDROCEPHALUS

[76] Inventor: Abdul Mateen Ahmed, 928 East Juanita Ave., La Verne, Calif. 91750

[21] Appl. No.: 592,016

[22] Filed: Jan. 26, 1996

Related U.S. Application Data

[63] Continuation-in-part of Ser. No. 269,839, Jul. 1, 1994, which is a continuation-in-part of Ser. No. 786,734, Oct. 1, 1991, Pat. No. 5,411,473, which is a division of Ser. No. 478,655, Feb. 12, 1990, Pat. No. 5,071,408, which is a continuation-in-part of Ser. No. 255,070, Oct. 7, 1988, abandoned.

[51] Int. Cl.$^6$ .................................................. A61M 5/00
[52] U.S. Cl. ................................. 604/9; 604/8; 604/128
[58] Field of Search ................... 608/8, 9, 10; 604/153, 604/126, 128, 129

[56] References Cited

U.S. PATENT DOCUMENTS

| | | |
|---|---|---|
| 3,527,226 | 9/1970 | Hakim . |
| 3,601,128 | 8/1971 | Hakim . |
| 3,623,484 | 11/1971 | Schulte ......................... 604/8 |
| 3,654,932 | 4/1972 | Newkirk . |
| 3,690,323 | 9/1972 | Wortman ....................... 604/8 |
| 3,768,508 | 10/1973 | Schulte . |
| 3,827,439 | 8/1974 | Schulte et al. . |
| 4,103,689 | 8/1978 | Leighton . |
| 4,240,434 | 12/1980 | Newkirk . |
| 4,364,395 | 12/1982 | Redmond et al. . |
| 4,464,168 | 8/1984 | Redmond et al. . |
| 4,554,918 | 11/1985 | White . |
| 4,560,375 | 12/1985 | Schulte ......................... 604/8 |
| 4,588,394 | 5/1986 | Schult et al. . |
| 4,681,560 | 7/1987 | Schulte et al. . |
| 4,741,730 | 5/1988 | Dormandy, Jr. ............... 604/8 |
| 4,850,955 | 7/1989 | Newkirk ....................... 604/8 |
| 4,898,583 | 2/1990 | Borsanyi et al. . |
| 4,898,584 | 2/1990 | Borsanyi et al. . |
| 4,898,585 | 2/1990 | Borsanyi et al. . |
| 5,152,753 | 10/1992 | Laquette .................... 604/153 |

OTHER PUBLICATIONS

Burr Hole Valve, Radionics; 12 pages.
Cardiac/Peritoneal Catheters; Radionics; 2 pages.
ICP Tele–Sensor; Radionics; 4 pages.
Neonatal Shunt Valve; Radionics; 2 pages.
Ventricular Catheters; Radionics, 2 pages.

*Primary Examiner*—Sam Rimell
*Assistant Examiner*—Luke Yeh
*Attorney, Agent, or Firm*—John J. Connors; Connors & Assoc

[57] ABSTRACT

Disclosed is a medical device comprising an external, flexible shell forming a fluid reservoir and housing a non-obstructive, self-regulating valve, having a folded membrane which forms a slit-like opening in a chamber. An inlet tube in communication with the chamber through an aperture in the membrane extends outwardly through an opening in the shell. The free end of the inlet tube, including holes, is in communication with the brain or cranial vault. There is an outlet tube in communication with the reservoir. The free end of the outlet tube, also including holes, is in communication with either the heart or the abdomen. If the outlet tube is in communication with the abdomen the preferred configuration of the free end includes rigid fins. Also disclosed is a method of using this device to treat hydrocephalus and a process for making the device.

25 Claims, 12 Drawing Sheets

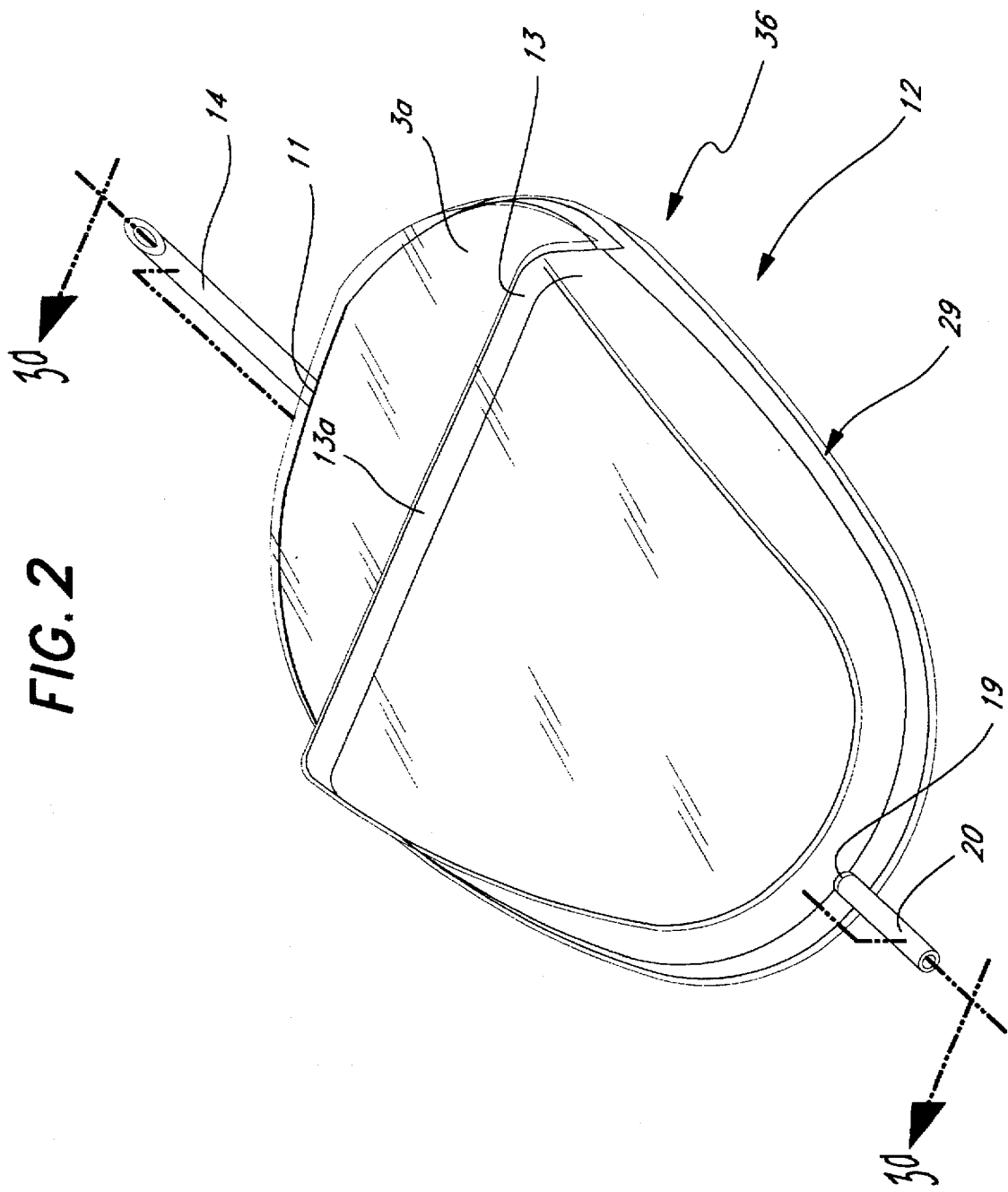

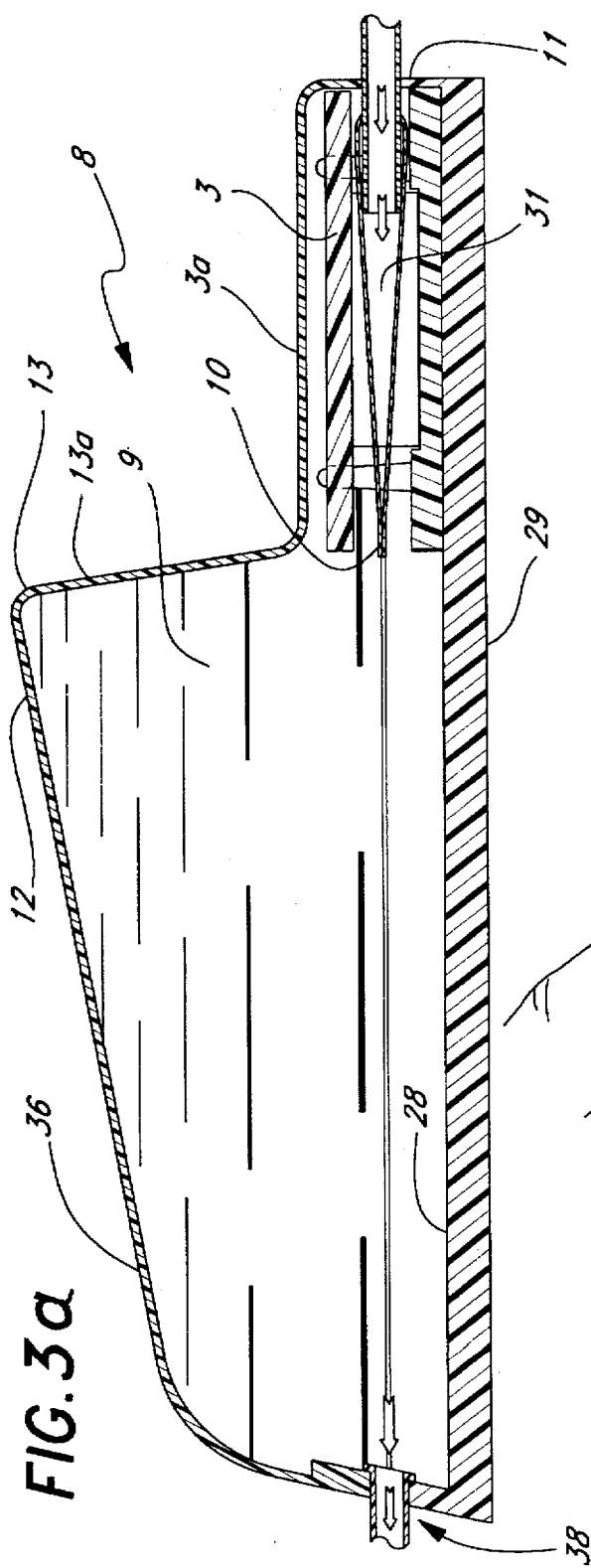
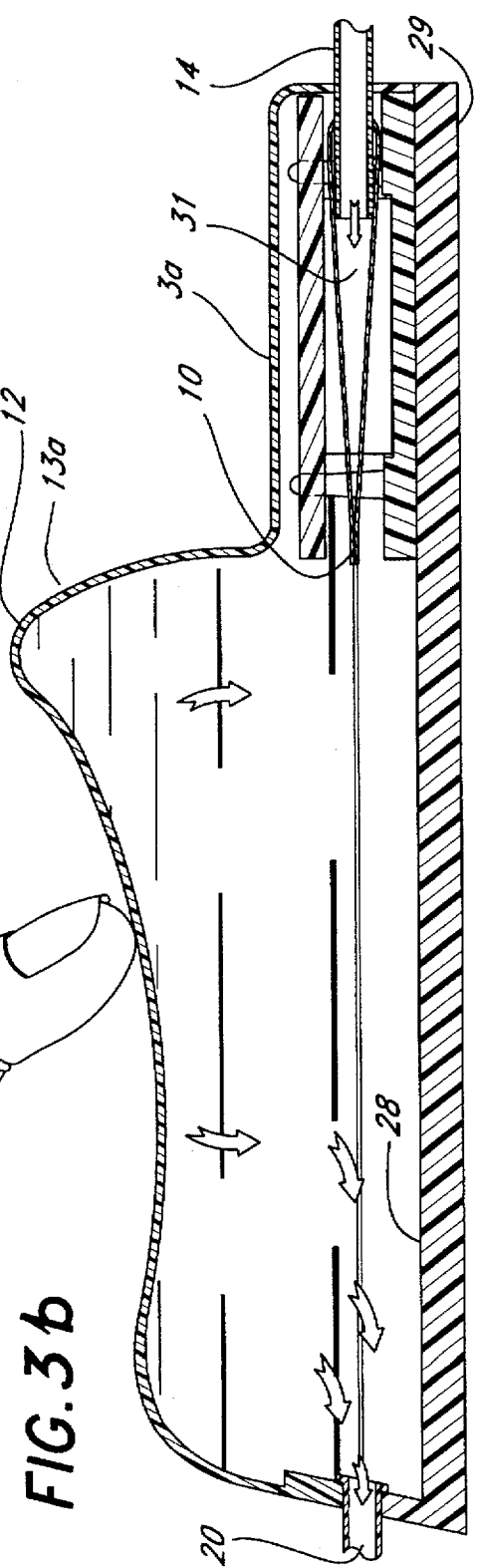

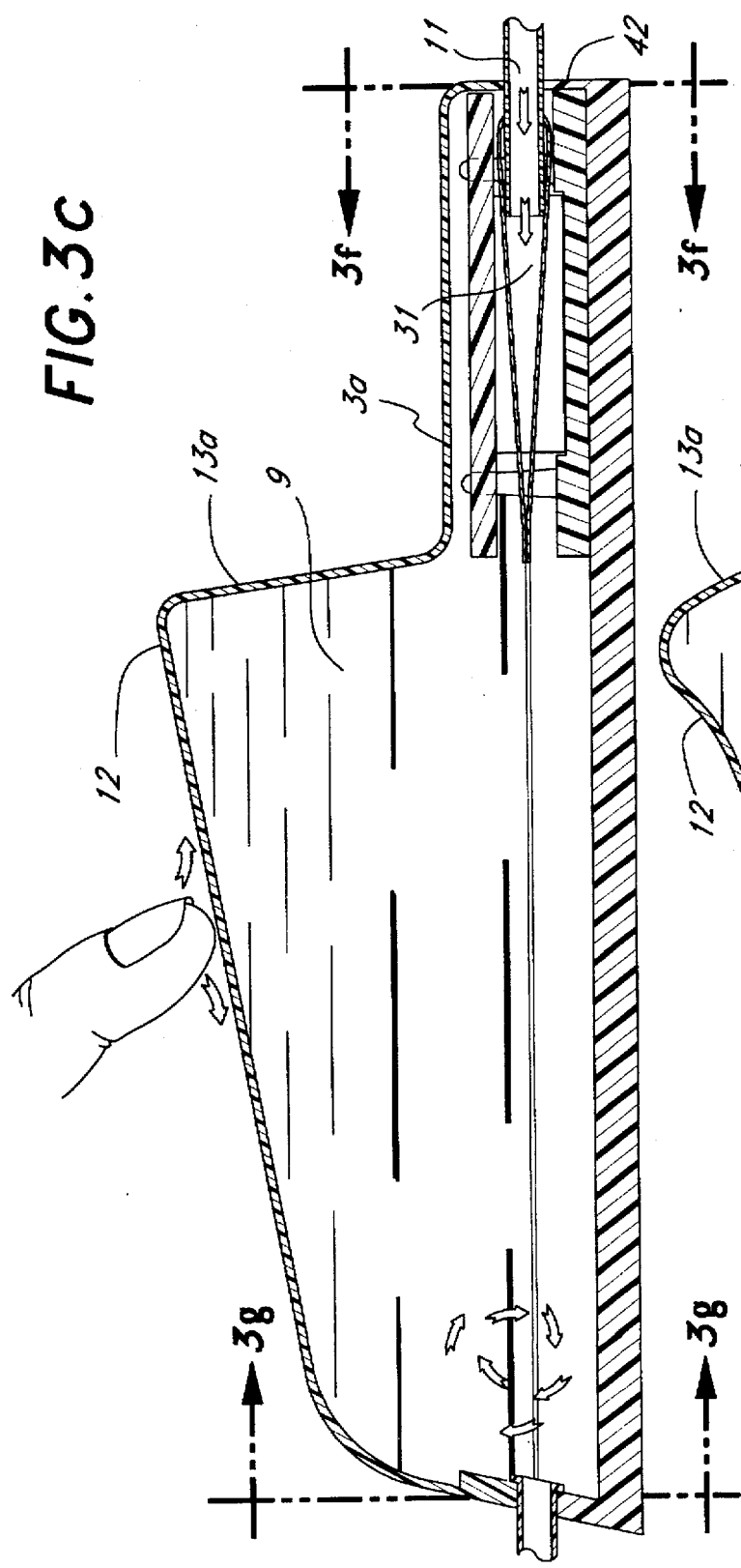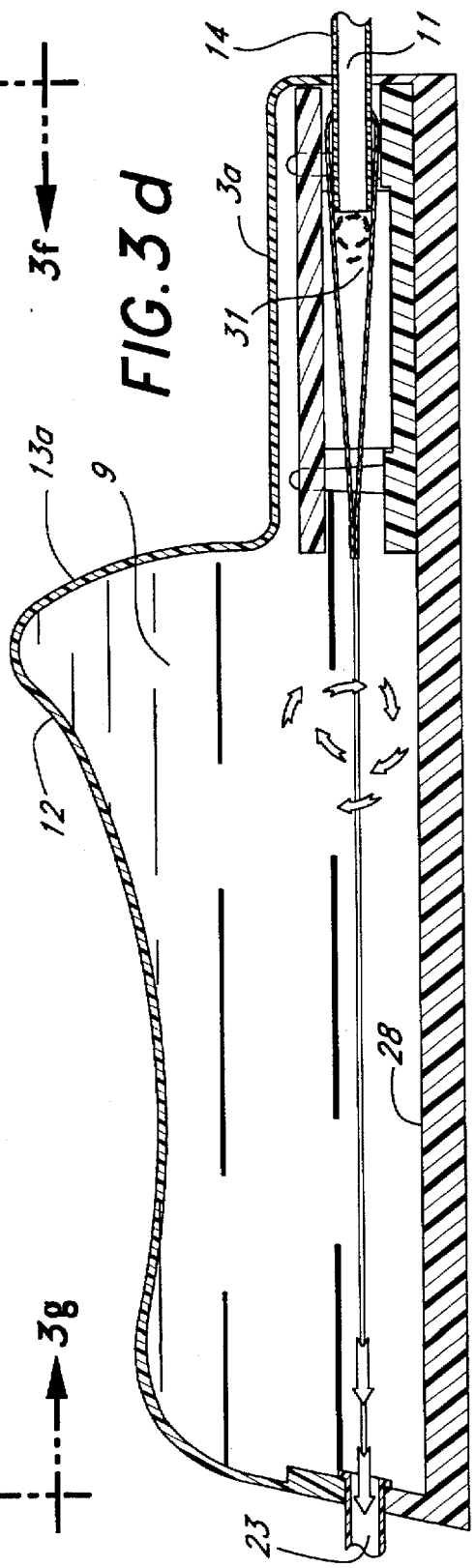

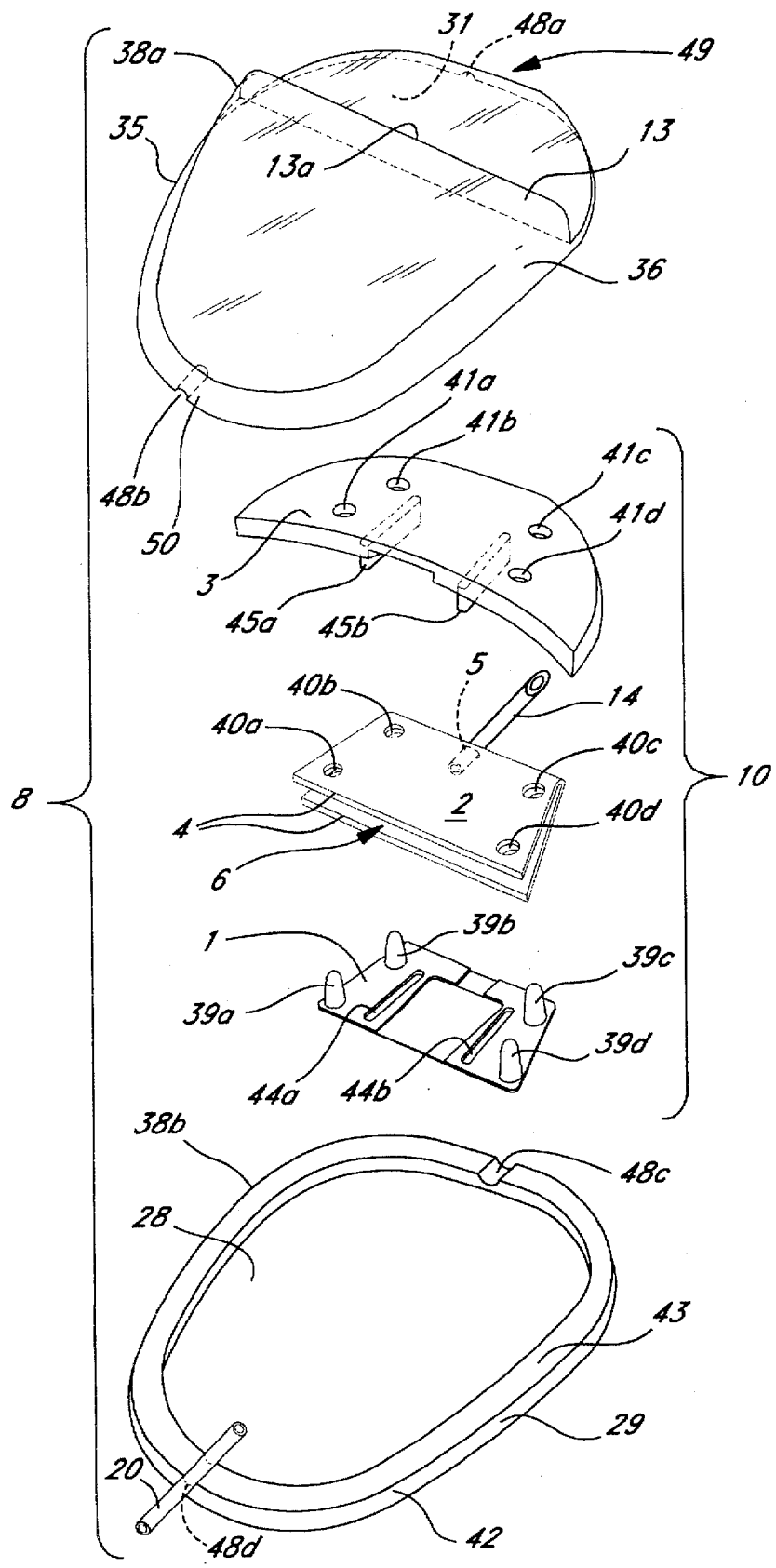

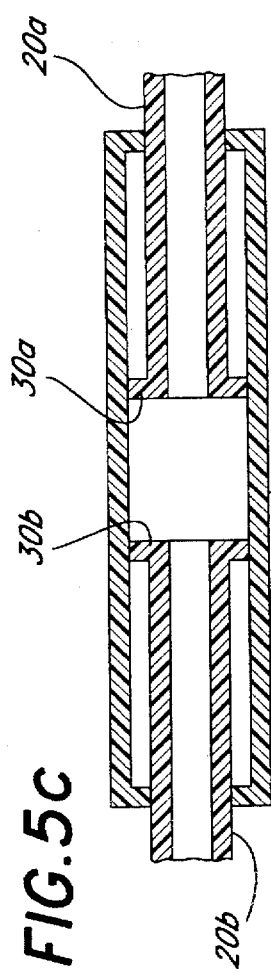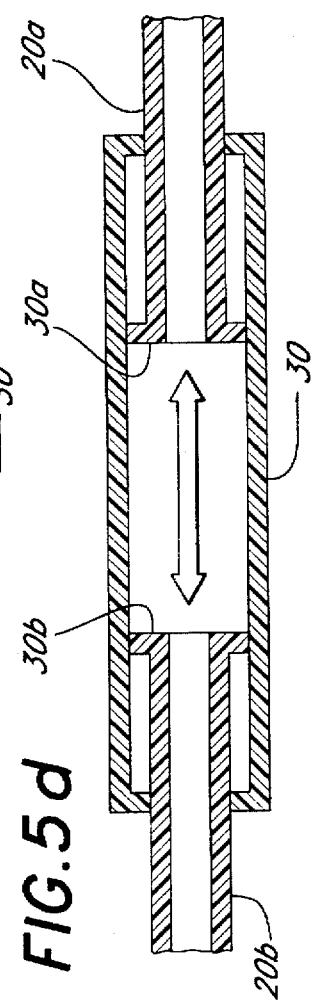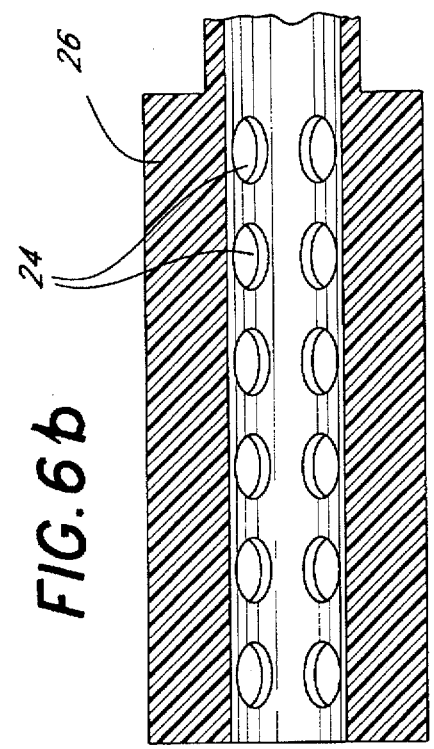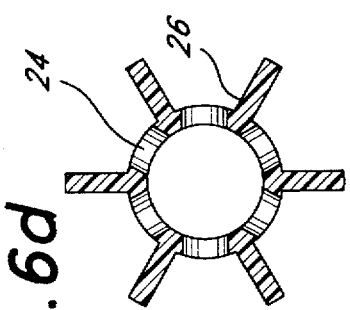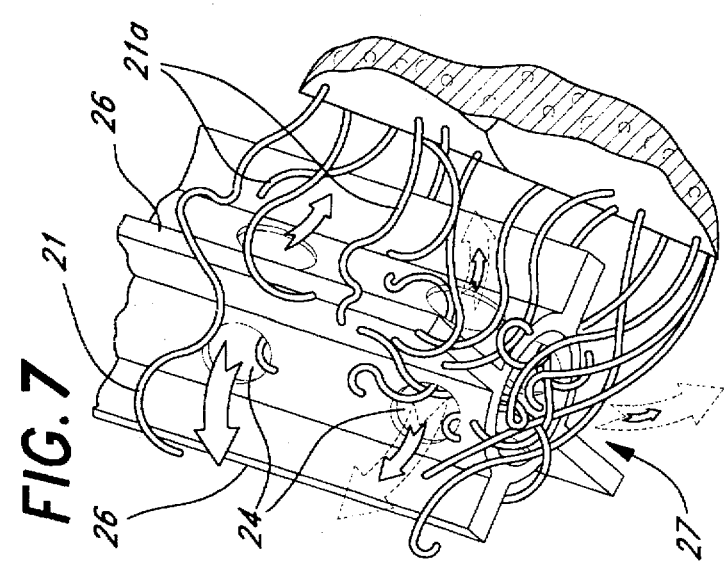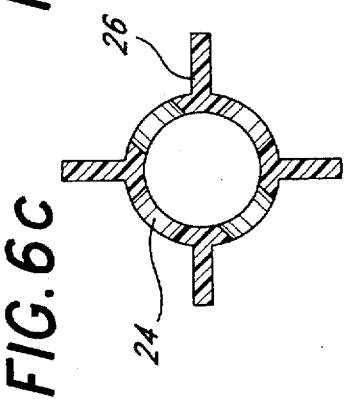

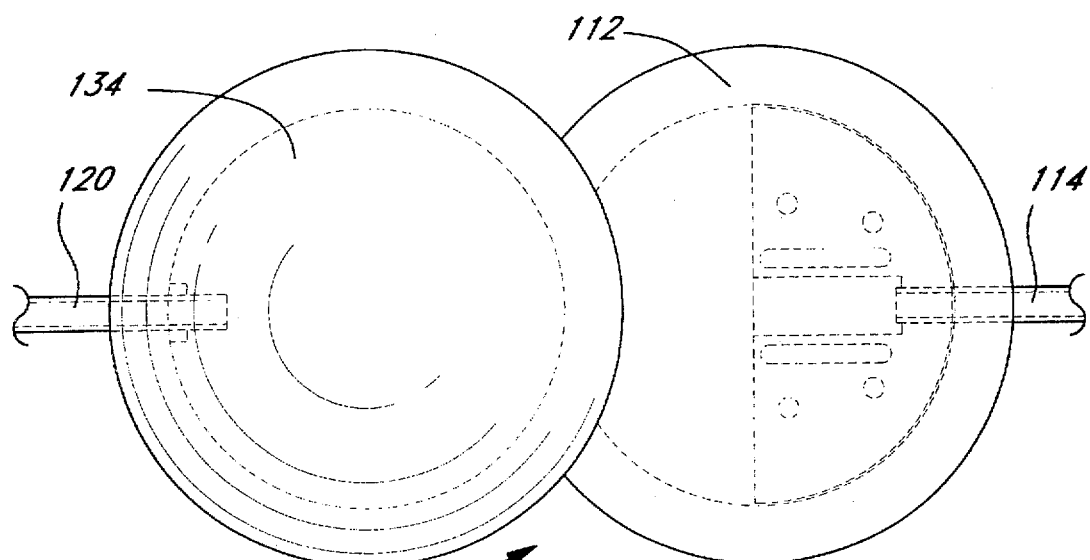
FIG. 10 a
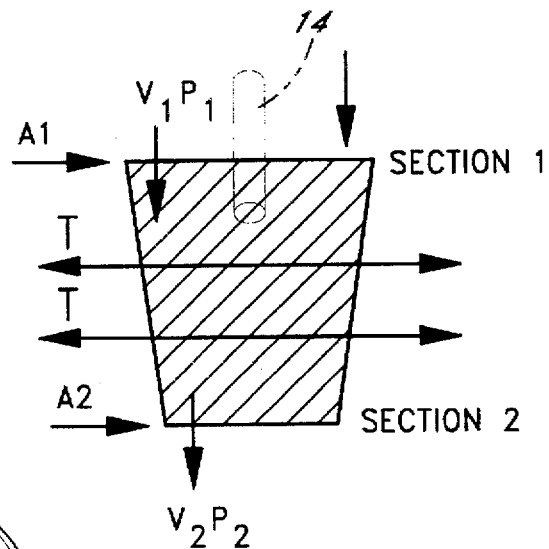
FIG. 12
FIG. 10 b
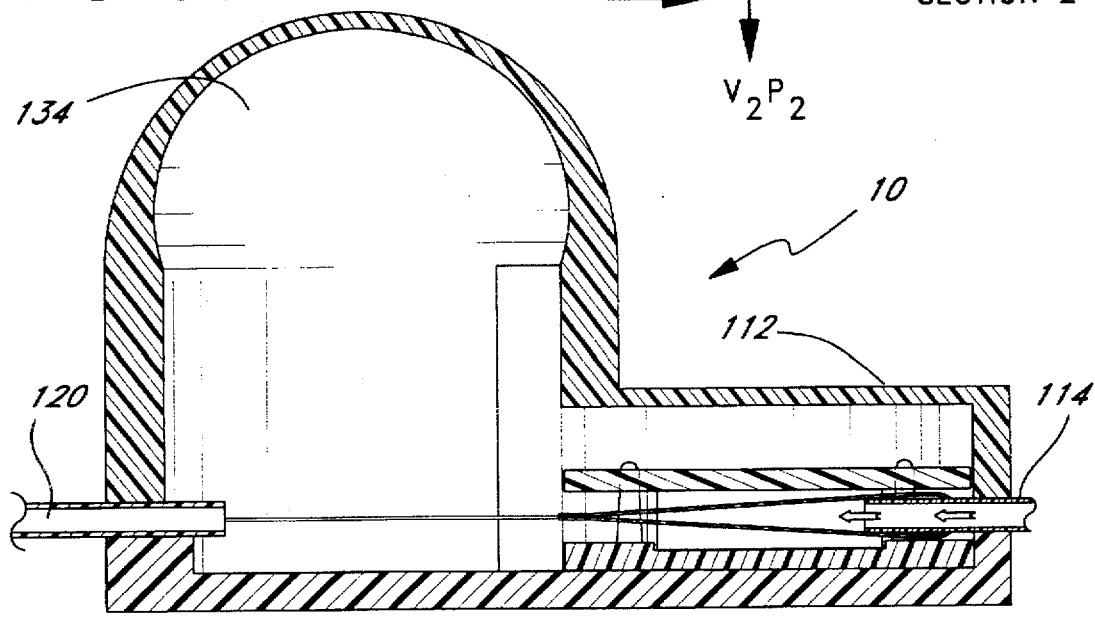

DEVICE AND METHOD FOR TREATING HYDROCEPHALUS

RELATED PATENT APPLICATIONS

This application is a continuation-in-part application of U.S. Ser. No. 08/269,839, entitled "Uniquely Shaped Ophthalmological Device," filed Jul. 1, 1994, which is continuation-in-part application of U.S. Ser. No. 07/786,734, entitled "Medical Valve," filed Oct. 1, 1991, now U.S. Pat. No. 5,411,473, which is a divisional application of U.S. Ser. No. 07/478,655, filed Feb. 12, 1990, and entitled "Medical Valve," now U.S. Pat. No. 5,071,408, which is continuation-in-part application of U.S. patent application Ser. No. 07/255,070, entitled "Self-Regulating Pressure Control Glaucoma Valve", filed Oct. 7, 1988 abandoned. All of these related applications are incorporated herein by reference and made a part of this application.

BACKGROUND OF THE INVENTION

FIELD OF INVENTION

This invention relates to medical devices which are implanted in the human body, and particularly, to a medical device used to treat hydrocephalus. "Hydrocephalus" is the diagnostic term meaning excess water in the brain or cranial vault due to the cerebral spinal fluid flow being blocked. When this occurs, the increased intracranial pressure causes the brain to flatten into a thin shell against the skull. In newborn babies this fluid pressure increase also causes the head to swell which, if left untreated, usually results in death.

BACKGROUND DISCUSSION

Medical valves are used for many different types of applications. As disclosed in U.S. Pat. No. 5,411,473, one type of valve (herein the Glaucoma Valve) has been used to treat glaucoma by allowing aqueous humor to flow from the intraocular chamber of the eye to relieve excess pressure. The Glaucoma Valve uses a membrane under tension to form its own fluid retention chamber. A slit-like opening is along adjoining, overlapping edges of portions of the membrane. The membrane responds to slight changes in fluid pressure and expands or contracts to open or close the opening. When opened, it provides a wide open mouth with parted lips that allows for free flow of fluid through it without any substantial resistance to fluid flow. This feature also substantially reduces the likelihood that the opening will be clogged by particulate matter.

SUMMARY OF THE INVENTION

In accordance with this invention, the Glaucoma Valve has been enclosed within a flexible shell to provide a medical device that may be used to treat hydrocephalus. This valve is especially suited for this application because its slit-like opening is not easily obstructed by particulates and it is self regulating, opening and closing in response to slight changes in pressure.

There are several features of this invention, no single one of which is solely responsible for its desirable attributes. Without limiting the scope of this invention as expressed by the claims, its more prominent features will now be discussed briefly. After considering this discussion, and particularly after reading the section of the application entitled "DETAILED DESCRIPTION OF THE PREFERRED EMBODIMENTS," one will understand how the features of this invention provide its benefits, which include the ability to self regulate drainage of fluid from a hydrocephalic brain into either the heart or the abdomen and further to ascertain when, whether, and where the device may have become blocked. The device is easy to manufacture, performs reliably, is easy to implant surgically in the human body, and will remain functional for the time required by the patient in which it is implanted.

The first feature of the medical device of this invention is that it is designed to treat a patient suffering from hydrocephalus. It includes a one-way flow valve having a membrane which forms a chamber with a slit-like opening. The chamber preferably has a trapezoidal configuration. The membrane has an aperture therein, and it is folded to form the slit-like opening. The membrane is maintained in tension by a pair of plates that are held together by means of a plurality of pins.

The second feature is that a flexible shell encloses the valve. The shell is injection molded from a bio-compatible, polymeric material and it provides a reservoir with first and second ends, each of these ends having openings therein. The shell expands or contracts in response to pressure.

The third feature is that the valve permits the flow of fluid in one direction only, allowing entry of fluid from the cranial vault of the patient through an inlet tube and the valve. This valve also prohibits the back flow of fluid from the reservoir up the inlet tube and back into the patient's brain. Because of the one-way valve, the drained cerebral-spinal fluid can only flow into the fluid reservoir and out an outlet tube.

The fourth feature is an inlet tube in communication with the valve through the aperture. The inlet tube has an end portion received by the opening at the first end of the shell, and a free end adapted to be inserted into the patient's head. The free end of the inlet tube has an open end and a plurality of holes adjacent this end.

The fifth feature is an outlet tube in communication with the reservoir. The outlet tube has one end portion received by the opening at the second end of the shell, and a free end adapted to be insert into the patient's body. The free end of the outlet tube is open, and there are a plurality of holes adjacent this open end. At the free end of the outlet tube, a rigid fin structure provides a site to collect omentum in an open structure that minimizes the possibility of blocking drainage. Depending upon the surgical preference and form of hydrocephalus diagnosed, the free end of the outlet tube may placed into either the heart or the abdomen to permit drainage from the fluid reservoir of the cerebral-spinal fluid. If the outlet tube is to be placed in the abdomen, the free end of the outlet line employs the rigid fin structure. This rigid fin structure is to further facilitate fluid drainage by helping to prevent the problem of the outlet tubing becoming clogged due to the growth of omentum from within the abdominal cavity. Without this fin structure, omentum may establish a residency upon the openings of the tube and thereby prevent drainage of fluid. Thus, openings remain essentially unobstructed during use. Preferably, the outlet tube has a telescoping section. This feature accommodates the needs of a growing hydrocephalic child without the need to resort to additional surgical procedures.

The sixth feature is that the shell is compressed when external pressure is applied to it to flush the device. If the shell resists compression, then the outlet tube is blocked. If the shell remains compressed after removing the externally applied compressive force, then the inlet tube is blocked. This may require replacement. By manually pushing on the top cover member of the shell, the user will be able to ascertain whether or not, either the inlet or outlet tube, is clogged or blocked. The manner in which the top cover member responds to manually applied pressure will inform the user whether the blockage is in the inlet tube or the outlet tube. If the inlet tube is blocked, the reservoir remains compressed upon the manual pressure being removed. If the outlet tube is blocked, the fluid reservoir resists compression and remains fully expanded.

This invention also includes a method for treating hydrocephalus by draining the fluid from the cranial vault of a patient, and a process for making a medical device.

This method for treating hydrocephalus includes the steps of:
(a) providing a medical device, including
   a valve having a membrane which forms a slit-like opening, said membrane having an aperture therein,
   a flexible shell which encloses the valve, the shell having an reservoir and first and second ends, with the first and second ends having openings therein,
   an inlet tube in communication with the valve through the aperture, the inlet tube having an end portion received by the opening at the first end of the shell, and a free end adapted to be inserted into the cranial vault, and
   an outlet tube in communication with the reservoir, the outlet tube having one end portion received by the opening at the second end of the shell, and a free end adapted to be insert into the patient's body.
(b) attaching the medical device to the patient with the flexible shell facing outward,
(c) inserting the free end of inlet tube into the cranial vault to enable fluid to drain through the free end of the inlet tube into the reservoir in the medical device,
(d) inserting the free end of the outlet tube into the patient's body to enable fluid to drain from the reservoir into the body of the patient.

The process for making a medical device includes the steps of:
(a) providing a top cover member and a base plate member which upon being connect form a flexible shell,
(b) providing a one-way directional flow device disposed between the top cover member and the base plate member prior to forming the shell,
(c) connecting the top cover member and the base plate member to enclosed the one-way directional flow device within the shell,
(d) providing an inlet tube and an outlet tube, and connecting the inlet tube to the one-way directional flow device and connecting the outlet tube to the shell.

DESCRIPTION OF THE DRAWING

The preferred embodiments of this invention illustrating all of its features will now be discussed in detail. These embodiments depicts the novel and unobvious features of the medical device of this invention. The drawing accompanying this application, which is for illustrative purposes only, includes the following figures (FIG.), with like numerals indicating like parts:

FIG. 2 is a perspective view of the medical device of this invention.

FIG. 3a is a cross-sectional view taken along line 3a—3a of FIG. 2.

FIG. 3b is a cross-sectional view similar to that shown in FIG 3a, with the shell of the medical device being manually depressed.

FIG. 3c is a cross-sectional view similar to that shown in FIG 3a, showing the inability to depress manually a filled device when there is an obstruction in the outlet tube.

FIG. 3d is a cross-sectional view similar to that shown in FIG 3a, showing the fluid reservoir remaining in the depressed state indicating an obstruction in the inlet tube.

FIG. 3e is an exploded perspective view of the medical device of this invention.

FIG. 5c is a cross-sectional view taken along line 5c—5c of FIG. 5a.

FIG. 5d is a cross-sectional view taken along line 5d—5d of FIG. 5b.

FIG. 6b is a cross-sectional view taken along line 6b—6b of FIG. 6a.

FIG. 6c is a cross-sectional view taken along line 6c—6c of FIG. 6a.

FIG. 6d is a cross-sectional view of an alternate structure for the end of the outlet tube.

FIG. 7 is a perspective view showing a rigid fin structure at the end of the outlet tube which prevents omentum from blocking the outward flow of fluid from the tube.

FIG. 10a is a cross-sectional view taken along line 10a—10a of FIG. 9.

FIG. 10b is a cross-sectional view taken along line 10b—10b of FIG. 9.

FIG. 12 is a schematic drawing illustrating the flow characteristics of the valve used in this invention.

DETAILED DESCRIPTION OF THE PREFERRED EMBODIMENTS

Figure 1:
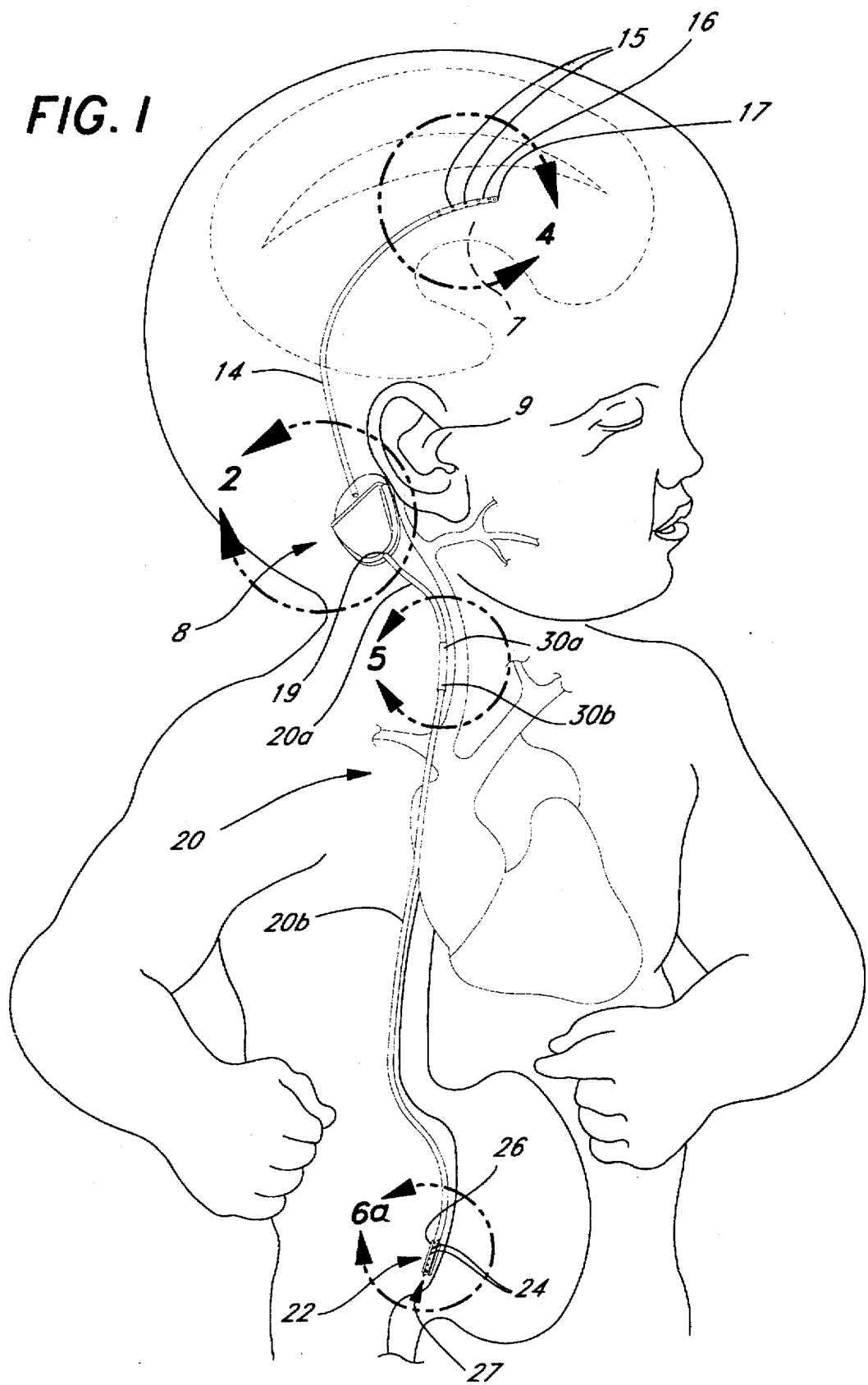
FIG. 1 is a schematic drawing depicting the medical device of this invention connected to a patient, showing the ventricular end of an inlet tube implanted into the brain of a patient and the peritoneal end of an outlet tube implanted into the abdomen of the patient.

As best illustrated in FIG. 3e, the medical device 8 of this invention includes a one-way directional flow valve 10, a base plate 29, and a top cover 36. The base plate 29 and top cover 36 are bonded together using an adhesive to form an external shell 12 (FIG. 3a) which houses the valve 10. There is an inlet tube 14 connected to the valve 10 and an outlet tube 20 extending from the shell 12.

The Valve

The valve 10 includes a bottom plate 1, a flexible, siliconized rubber membrane 2, and a top plate 3. The membrane 2 is originally in a non-folded condition and it has an hourglass-like shape narrowing at a central section and then expanding outwardly there from in both directions. The membrane 2 has a thickness ranging between 0.004 inches and 0.007 inches, preferably between 0.005 inches and 0.006 inches. The membrane is folded along a center line (not shown) and there is an aperture 5 in the membrane 2 along this center line in which the inlet tube 14 is inserted. A medical grade, bio-compatible adhesive is used to bond the inlet tube 14 to the aperture 5 of the membrane 2.

To assemble the valve 10, the membrane 2 is first folded as shown in FIG. 3e. The overlapping edges 4 of the folded membrane 2 create between the two halves of the membrane 2 an internal chamber 31 upon assembly of the valve and a slit 6 at the end of this chamber opposite an elongated opening. In response to a predetermined pressure within the chamber 31, fluid will then pass through the slit 6. Tension is applied to the overlapping edges 4 to maintain the slit 6 in a normally closed state. This enables the valve 10 to function as a one-way directional flow device. To create this tension, the folded membrane 2 is stretched and placed between the top plate 3 and the bottom plate 1 to hold the stretched membrane in tension. Next, the folded membrane 2 is placed between precisely aligned and spaced apart top plate 3 and a bottom plate 1. These plates 1 and 3, with the membrane 2 stretched and sandwiched between them, are pressed together and interlocked by pins 39a, 39b, 39c, 39d in the bottom plate 1 which pass through holes 40a, 40b, 40c, and 40d in the membrane and bores 41a, 41b, 41c, 41d in the top plate 3. Grooves 44a and 44b in the bottom plate 1 and fingers 45a and 45b in the top plate 3 interlock and clamp the folded membrane 2 firmly between the top plate 3 and the bottom plate 1. Ultrasonic welding is used to bond the bottom plate 1 and the top plate 3 together. The valve 10 is assembled with the inlet tube 14 affixed to the membrane 2.

Non-Obstructive Feature of the Valve

As illustrated in FIG. 12, the two halves of the membrane 2 have been configured to form a closed trapezoidal section with one end blocked, except for the inlet tube 14, and the other end parted into the slit 6. This unique feature is not present in any existing one-way valve mechanisms. Most of the conventional valves are designed as slit valves, or valves with a spring to keep them closed. In this unique design of the valve 10, the fluid flow has no physical restriction in its path of flow. The closing function of the valve is achieved by providing a pre-determined tension to be applied physically to the membranes. This tension can be varied according to the desired design requirements by increasing or decreasing the depth of the fingers 45a and 45b in the grooves 44a and 44b.

The use of the member in tension in the valve 10 helps to keep it unobstructed at all times. For example, in case of meningitis, the infection in C.S.F. (Cerebro-Spinal Fluid) causes the C.F.S. to become more viscous. Most of the slit valves will not open easily when the viscosity and surface tension of the fluid changes. This is not the case with this invention. In the ophthalmic use of the valve 10, it has been reported that even a fluid 10 times thicker than water, namely, methyl cellulose, could easily pass through this non-obstructive valve. The non-obstructive quality of the valve 10 makes it very sensitive to even small pressure changes.

Unique Flow Characteristics of the Valve

Most of the existing designs of valves used in the human body create a resistance in the path of the flow. Many times the need to have a variable flow valve is necessary as in the case of hydrocephalus. For example, a child has smaller ventricles, yet it is critical to lower the high intracranial pressure immediately so that it would not compress the dura mater of the brain. In the adult condition, the fluid has to be drained in much larger volumes but at a slower rate. These two conditions warrant variable pressure valves.

The valve 10 provides a venturi because of its trapezoidal configuration which makes the valve a variable pressure valve. This can be demonstrated by using Bernoulli's Equation. Referring to FIG. 12, taking at the inlet a section Section 1 of the valve 10, there is a large area A1, the fluid velocity is $V_1$ and pressure is $P_1$; and taking at the outlet another section Section 2 of the valve 10, there is a smaller area $A_2$, the fluid velocity is $V_2$ and the pressure is $P_2$.

Since the fluid that is coming into any part of Sections 1 and 2 is incompressible, whatever fluid comes into any section at unit time must leave that same section in unit time. This is the Theorem of Continuity. The membranes that make up this trapezoidal section are in tension created by the fingers 45a and 45b; the tension here is shown as T. Over the entire cross-sections, this tension is constant. The variable area of the sections of the valve makes this a self-controlling, self-adjusting valve with no external means required to change the flow or pressure.

Writing the Bernoulli's Equation between Section 1 and Section 2:

$$\frac{P_1}{W} + \frac{V_1^2}{2g} + Z_1 = \frac{P_2}{W} + \frac{V_2^2}{2g} + Z_2$$

where
- P1 is inlet pressure
- P2 is outlet pressure
- V1 is inlet velocity
- V2 is outlet velocity
- W is weight of fluid
- g is acceleration due to gravity
- Z1 and Z2 are static pressures from the datum. In this particular case, Z1=Z2

Taking all the pressure and velocity terms on one side of the equation, we get:

$$\frac{P_1}{W} - \frac{P_2}{W} = \frac{V_2^2}{2g} - \frac{V_1^2}{2g}$$

$$\frac{P_1 - P_2}{W} = \frac{V_2^2 - V_1^2}{2g}$$

$$P_1 - P_2 = \frac{W}{2g} [V_2^2 - V_1^2]$$

Since W/2g is a constant $P_1 - P_2 \alpha\ V_2^2 - V_1^2$

In other words, a very small difference in pressure between any two sections of the trapezoid leads to a greater flow. To explain this further, assuming $P_1=10$ mm Hg, $P_2=5$ mm Hg. $V_1=5$ µl/min and $V_2=10$µl/mt.

$$P_1 - P_2 \quad \alpha \quad V_2^2 - V_1^2$$
$$10 - 5 \quad \alpha \quad 10^2 - 5^2$$
$$5 \quad \alpha \quad 100 - 25 = 75$$

For a small pressure difference of 5, the velocity difference becomes 75. Now if $P'_1$ became 15 and $P'_2$ 10 and $V'_2$ 15 and $V'_1$ 10.

$$P'_1 - P'_2 \qquad V_2^2 - V_1^2$$
$$10 - 5 \qquad (15)^2 - (10)^2$$
$$5 \quad \alpha \quad 225 - 100$$
$$5 \qquad 125$$

For a difference of pressure of 5, the velocity difference is now 125. This demonstrates that the trapezoidal configuration providing a venturi for the valve 10 helps to change automatically the fluid flow characteristics of the valve without having to make any physical adjustments.

Construction and Operation of the Medical Device

As best depicted in FIGS. 2 and 3a through 3d, the top cover 36 and the base plate 29 have a generally ovoid shape and are made of a flexible material such as, for example, siliconized rubber. The top cover 36 and base plate 29 are made separately by injection molding. The top cover 36 and the base plate 29 are joined together to form the shell 12 which includes within it a fluid chamber 9. The top cover 36 is affixed to the base plate 29 of the shell 12 along the perimeters 38 of the top cover 36 and the base plate 29. As illustrated in FIG. 3a, the inlet tube 14 is affixed to the valve 10 located in the first end 11 of the base plate 29, and the outlet tube 20 is affixed to the shell 12 and in communication with the fluid chamber 9.

Figure 3F:
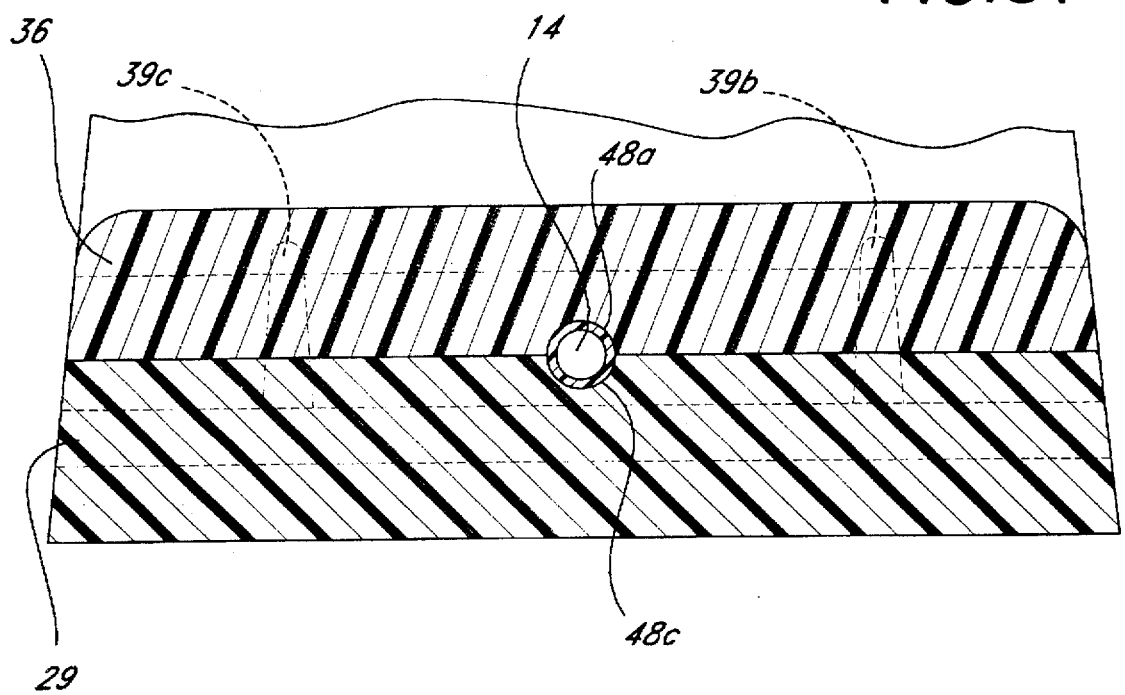
FIG. 3f is a fragmentary, sectional view taken along line 3f—3f of FIG. 3c.
Figure 3G:
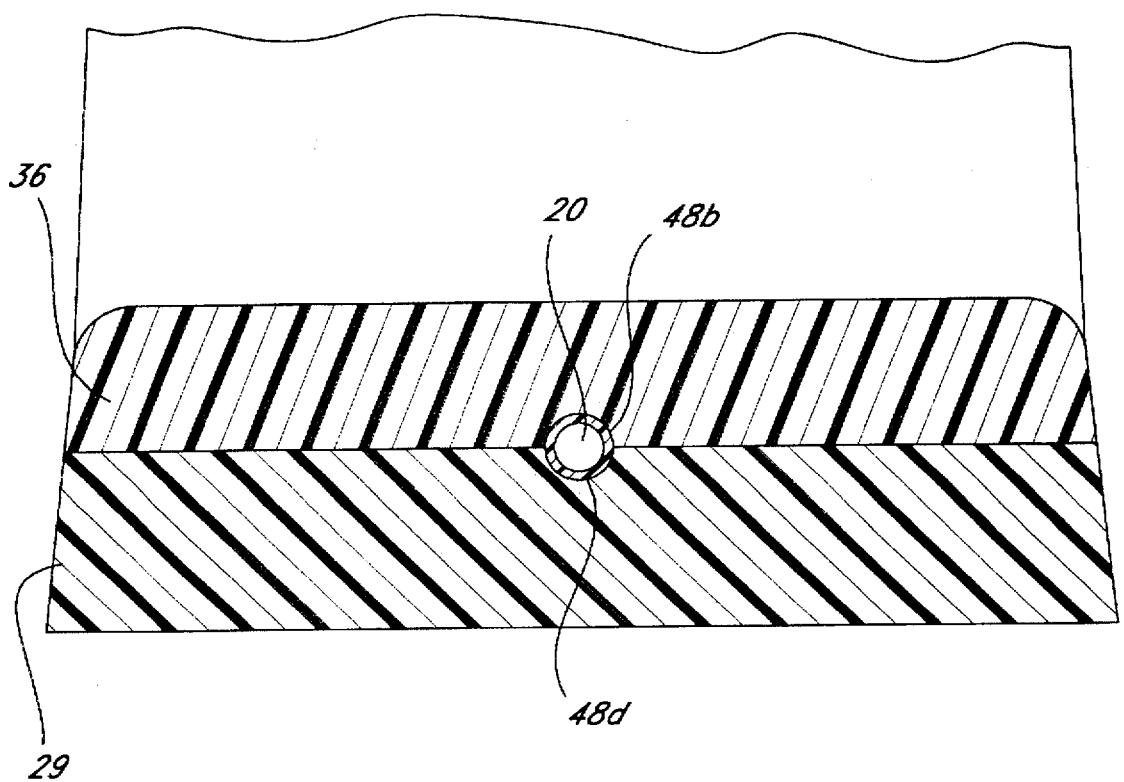
FIG. 3g is a fragmentary, sectional view taken along line 3g—3g of FIG. 3c.

As best depicted in FIGS. 3f and 3g, there are opposed, semicircular, molded openings 48a and 48b, respectively, at the forward end 49 and the rear end 50 along the outside edge 35 of the top cover 36. The base plate 29 has a generally flat central portion 28 surrounded by a raised rim 42 which has an upper edge 43. There are opposed, semicircular, molded openings 48c and 48d, respectively, at the forward end 18 and the rear end 19 along the rim 42 of the base plate 29. Upon assembly of the top cover 36 and the base plate 29, the ends of the inlet tube 14 and outlet tube 20 are seated in these openings 48a and 48b, and 48c and 48d.

The top cover 36, preferably, has a raised surface 13 that includes a step 13a in its upper portion that merges with a land 3a that is above the valve 10 enclosed within the shell 12. The top cover 36 turns at an approximate 90° degree angle to create the step 13a which then turns and gently slopes into the land 3a.

The valve 10 is positioned between the top cover 36 and the base plate 29 and then these components are assembled. As best shown in FIG. 3f, an end portion 11 of the inlet tube 14 is wedged between the semi-circular opening 48a in the top cover 36 and the semi-circular opening 48c in the base plate 29. As best shown in FIG. 3g, an end portion 23 of the outlet tube 20 is wedged between the semi-circular opening 48b in the top cover 36 and the semi-circular opening 48d in the base plate 29. The top cover 36 and the base plate 29 are positioned so that the edge 35 of the top cover and the edge 43 of the base plate 29 abut. These edges 35 and 43 are glued together to create a reservoir 9 within the shell 12. The top cover 36, the base plate 29, the inlet tube 14 and the outlet tube 20 are held in place with a medical grade, biocompatible adhesive.

Figure 4:
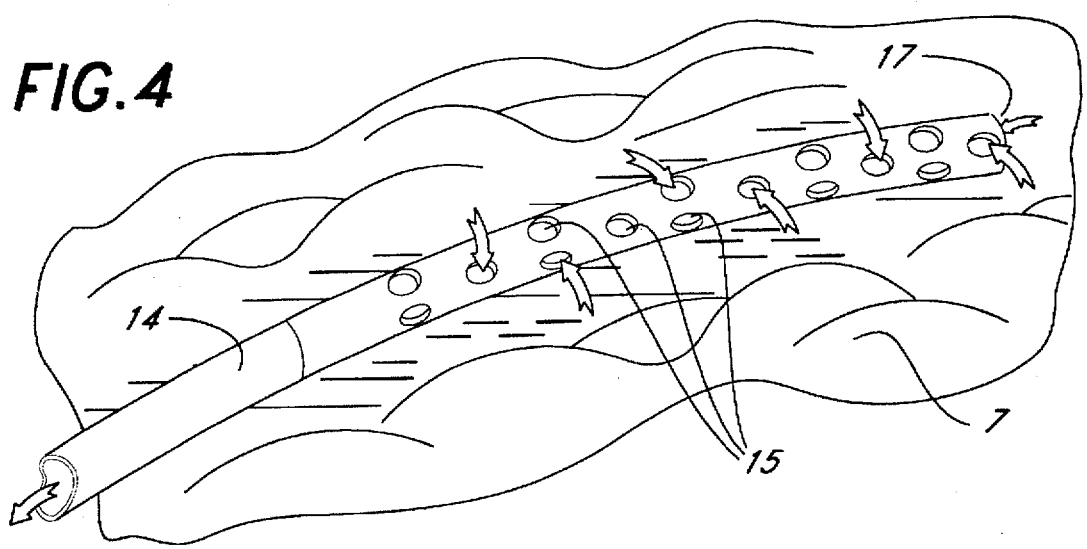
FIG. 4 is a fragmentary, perspective view showing the free end of the inlet tube in the brain.
Figure 5A:
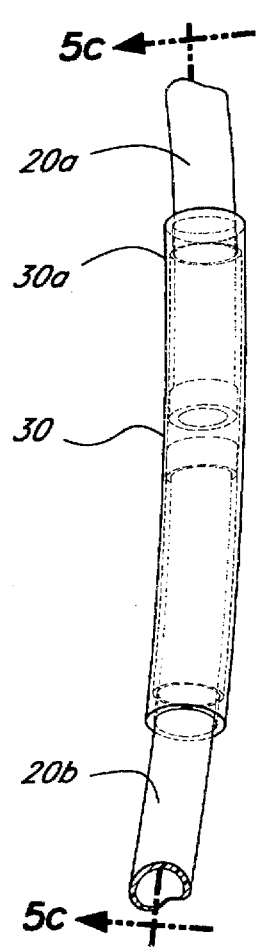
FIG. 5a is a perspective view of a portion of the outlet tube showing a telescoping feature with the outlet tube compressed.
Figure 5B:
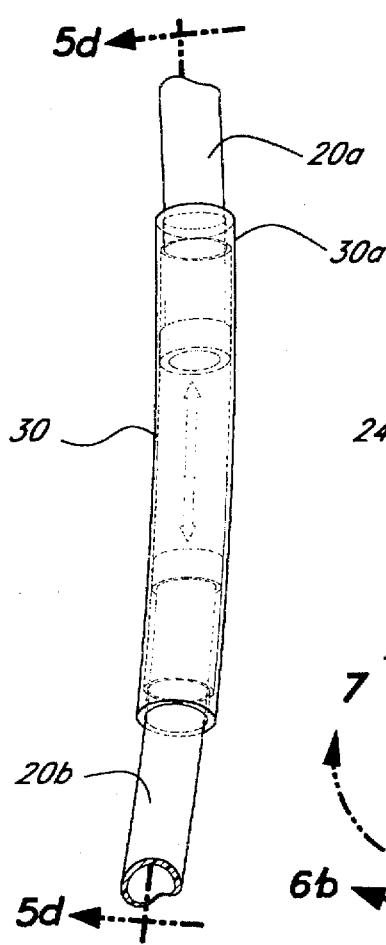
FIG. 5b is a perspective view similar to FIG. 5a showing the telescoping feature of the outlet tube when the tube is expanded.

FIGS. 1 and 4 show the surgical implantation of the inlet tube 14 into the brain 7 of a patient. The inlet tube 14 has a free end 16 which is open at the tip 17. There may be adjacent the tip 17 a plurality of holes 15 for removing excess cerebral spinal fluid. In response to elevated intracranial pressure in excess of 15 millimeters (mm) of mercury (Hg), fluid enters the holes 15 of the inlet tube 14 and flows through the tube 14 into the valve 10. The fluid fills the chamber 31, causing the pressure within the chamber to increase. When the intracranial pressure exceeds 15 millimeters (mm) of mercury (Hg), the pressure within the chamber 31 causes the slit 6 in the folded membrane 2 to part, permitting the excess fluid to flow into the reservoir 9 of the shell 12. When the intracranial pressure is reduced to between about 5 and about 10 mm Hg, the pressure is insufficient to cause the parting of the slit 6. This allows the valve 10 to operate as a check valve, preventing fluid flow from the reservoir 9 to the brain 7.

FIG. 1 and FIGS. 5a, 5b, 5c and 5d illustrate the telescoping feature 30 of the outlet tube 20. The outlet tube 20 has two segments 20a and 20b which each include a piston shaped ends 30a and 30b. These ends 30a and 30b fit snug within the housing 30, and slide along the internal surface of the housing due to the pulling action on the segments 20a and 20b with growth of the patient. This feature allows a hydrocephalic child to grow without the need to replace the tubing, since the tubing will elongate to accommodate the child's growth. The segments 20a and 20b designed to snugly nest within the housing 30 permit extension of the outlet tube 20 longitudinally.

Figure 6A:
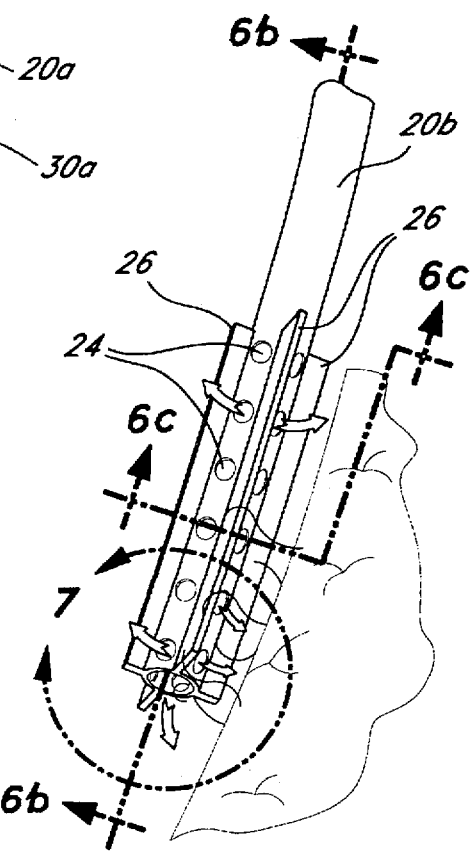
FIG. 6a is a fragmentary, perspective view showing the free end of the outlet tube used when the tube is placed in the abdomen.
Figure 8:
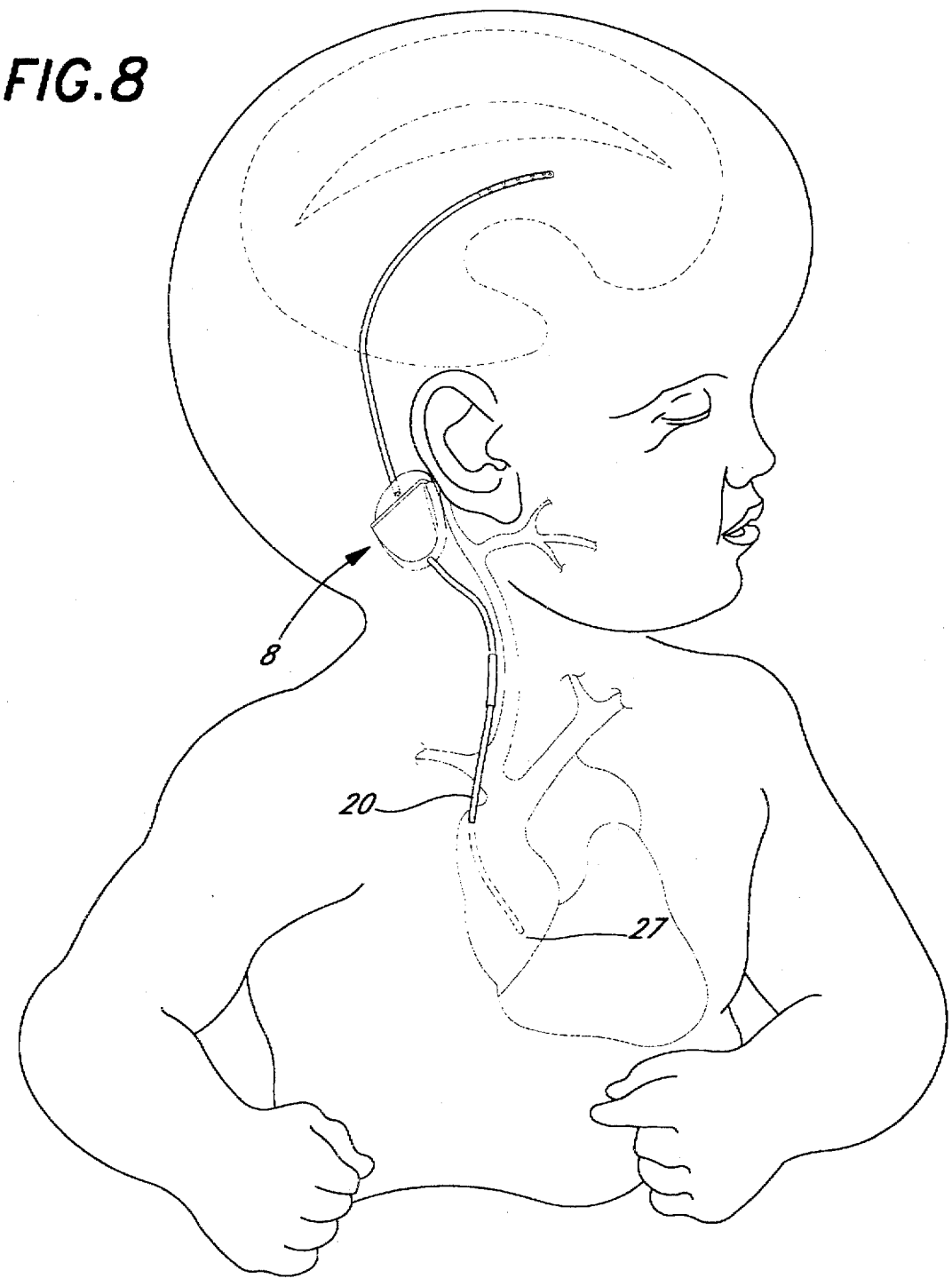
FIG. 8 is a perspective view of the medical device of this invention inserted into the heart of a patient.

The medical device is placed under the skin of the patient near the ear, and the outlet tube 20 may be insert into the abdomen (FIG. 1) or the heart (FIG. 8). As best illustrated in FIGS 6a through 6d, and FIG. 7, when the outlet tube 20 is inserted into the abdomen, there are a number of parallel rows of aligned holes 24 in the end of the segment 20b that facilitate draining of fluid from the shell 12 and parallel rigid fins 26 between these rows of holes. When the outlet tube 20 is inserted into the heart, the fins 26 are eliminated (FIG. 8). As best illustrated in FIGS. 6a through 6d, the rows of holes 24 and the fins 26 are generally parallel to the longitudinal axis of the outlet tube 20. The tip 27 of the free end 22 is open. FIGS. 6c and 6d illustrate different configurations of rigid fin 26 structures with variations in the number of fins.

As best depicted in FIG. 7, the rigid fins 26 prevent naturally occurring omentum 21 from blocking the outlet tube 20. The omentum 21 comprises strands 21a of material which are support by the fins 26 in an open structure. These rigid fins 26 assist in directing abdominal omentum 21 away from the opening 27 and the holes 24, thereby minimizing blockage or clogging of the holes 24 to allow fluid to flow through the open structure.

One highly desirable feature of the invention depicted in FIGS. 3b, 3c and 3d is the response of the external shell 12 to manual pressure. In FIG. 3b, the user pushes against the shell 12. If the outlet tube 20 is not blocked, the shell 12 is depressed and fluid exits the reservoir 9 as indicated pushing collected cerebral-spinal from the reservoir 9 via the outlet tube 20. Fluid cannot flow back into the inlet tube 14 because the valve 10 prohibits backward flow. This enables the user to flush periodically the reservoir 9 and tube 20.

FIG. 3c and FIG. 3d show the procedure used to determine if the assembly is blocked. FIG. 3c depicts resistance of the external shell 12 to manual pressure. This indicates a blockage in the outlet tube 20, prohibiting the free flow of fluid from the reservoir 9. When there is a blockage in the inlet tube 14, manual pressure applied to the shell 12 produces a compressed shell 12 which remains in this compressed condition when the manual pressure is removed as indicated in FIG. 3d. This compressed condition of the shell 12 is seen by the user as a contraction, dimpling, or depression in the skin opposite the shell 12.

Second alternate embodiment

Figure 9:
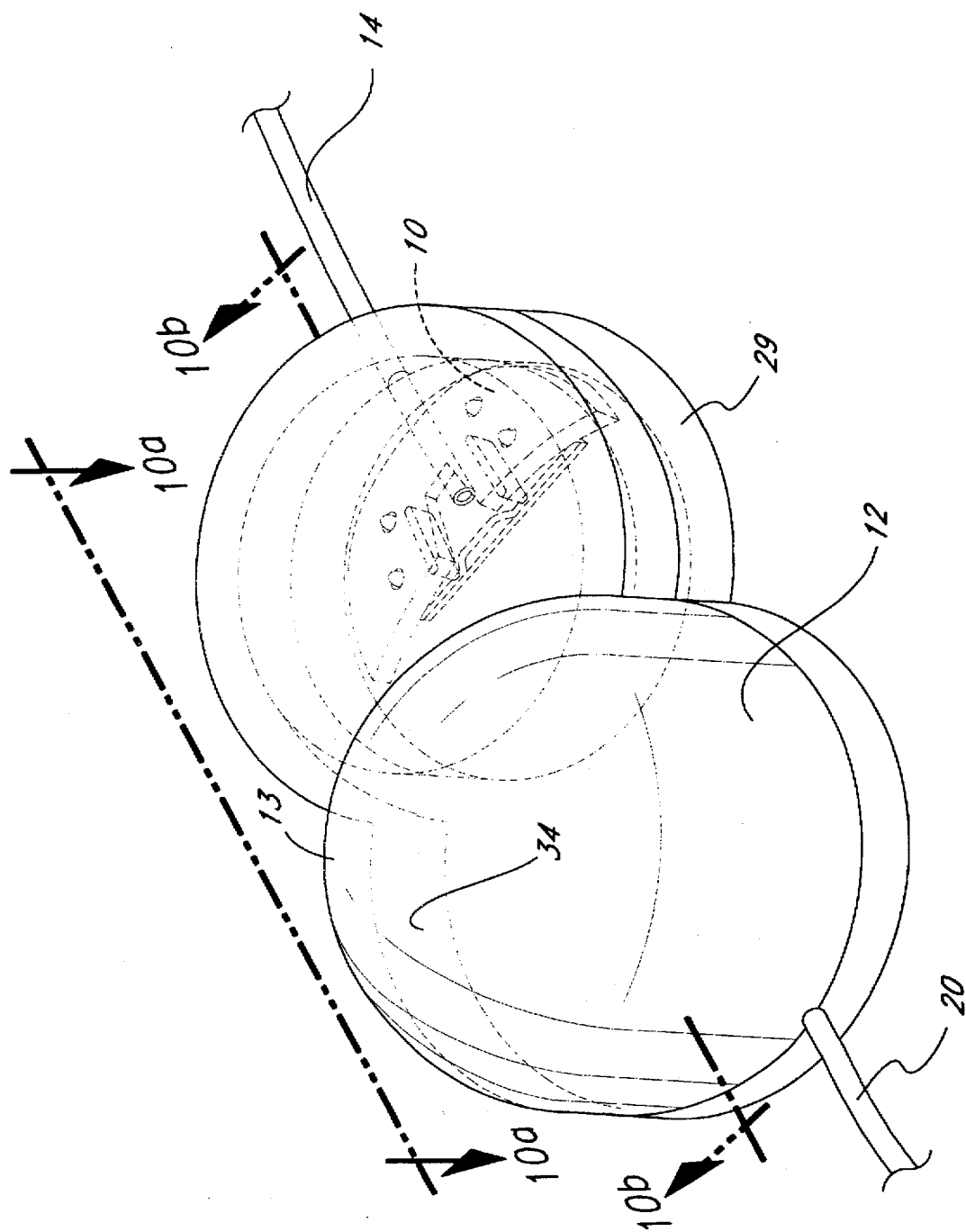
FIG. 9 is a perspective view of a second embodiment of the medical device of this invention.
Figure 11A:
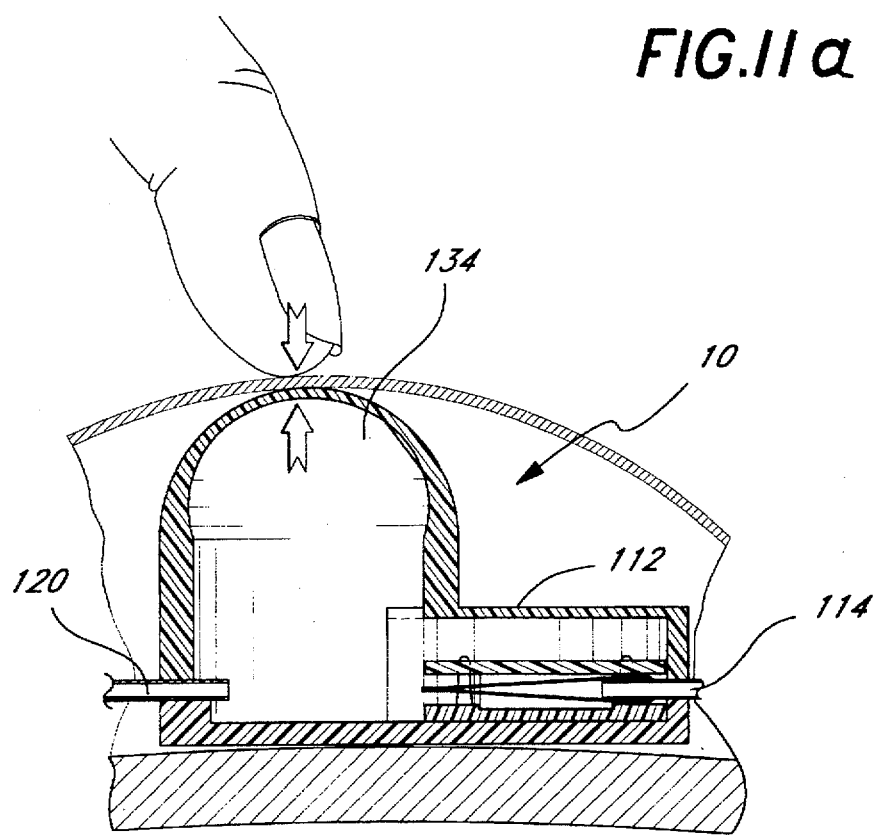
FIG. 11a is a cross-sectional view of the second embodiment of this invention showing the external shell resisting manual compression when the outlet tube is blocked.
Figure 11B:
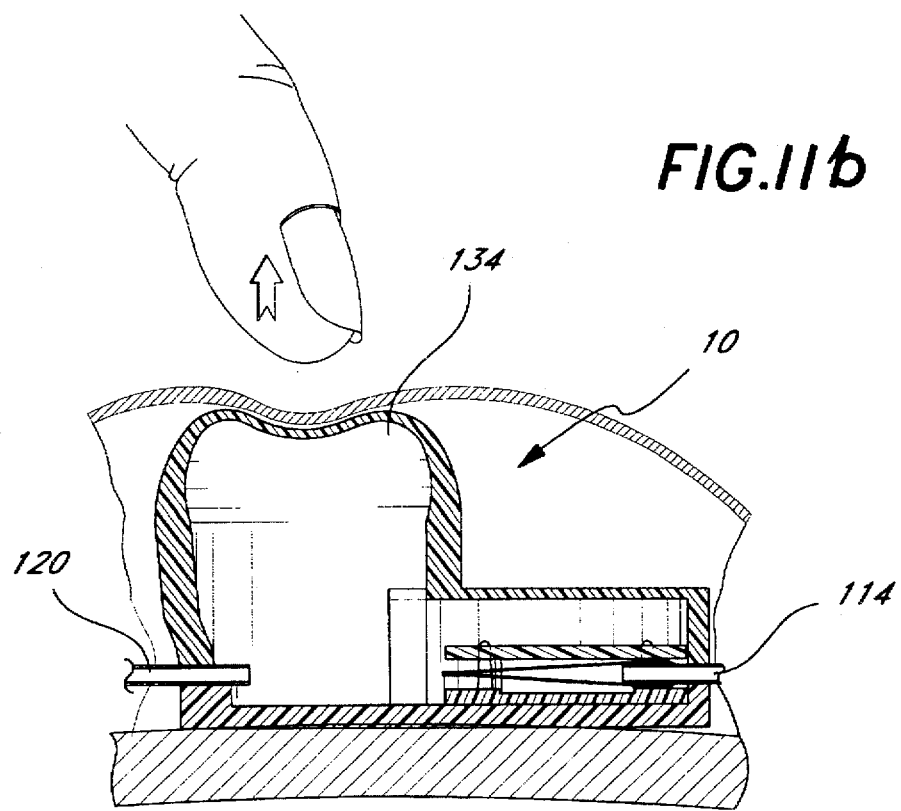
FIG. 11b is a cross-sectional view similar to that shown in FIG. 11a showing the external shell remaining compressed when the inlet tube is a blocked.

As depicted in FIGS. 9, 10a and 10b, the shell 12 housing the one-way directional flow device 10, may have various configurations. In this alternate embodiment, there is a flexible shell 112 which encloses the valve 10. There is an inlet tube 114 and the outlet tube 120 connected respectively to the valve 10 and the shell 112. The shell 112 is in the form of two adjacent and connected compartments in communication with each other. The one compartment is in the form of a rounded dome 134 adjacent to a relatively flatten circular structure which encloses the valve 10. The inlet and outlet tubes are connected in essentially the same manner as they where connected in the first embodiment of this invention.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiment disclosed. On the contrary, the intention is to cover all modifications and alternate constructions coming within the spirit and scope of the invention as generally expressed by the following claims, which particularly point out and distinctly claim the subject matter of the invention.

I claim:

1. A medical device for treating a patient suffering from hydrocephalus, including
    a valve having a membrane folded to form a slit-like opening, a pair of plates which maintain the folded membrane in tension, and an aperture therein displace from the slit-like opening,
    a flexible shell which encloses the valve, said shell having a reservoir and first and second ends, with said first and second ends having openings therein,
    an inlet tube in communication with the valve through the aperture, said inlet tube having an end portion received by the opening at the first end of the shell, and a free end adapted to be inserted into the patient's head, and
    an outlet tube in communication with the reservoir, said outlet tube having one end portion received by the opening at the second end of the shell, and a free end adapted to be insert into the patient's body.

2. The medical device of claim 1 where the shell is molded.

3. The medical device of claim 1 where the membrane is formed into a chamber having a trapezoidal configuration.

4. The medical device of claim 3 where the plates are held together by means of a plurality of pins.

5. The medical device of claim 1 where the shell expands or contracts in response to pressure.

6. The medical device of claim 1 where the valve is a one-way flow device.

7. The medical device of claim 1 where the free end of the inlet tube has a plurality of holes adjacent the free end.

8. The medical device of claim 1 wherein the free end of the outlet tube is open.

9. The medical device of claim 8 where there are a plurality of holes adjacent the free end.

10. The medical device of claim 1 wherein the free end of the outlet tube includes a rigid fin structure.

11. The medical device of claim 1 where the outlet tube has a pair of sections with one section within the other section and said sections adapted to slide telescopically.

12. The medical device of claim 1 where the shell is compressed when external pressure is applied to said shell.

13. The medical device of claims 12 where the shell resists compression when said outlet tube is blocked.

14. The medical device of claims 12 where said shell remains compressed when said inlet tube is blocked.

15. A medical device for draining fluids including
    a flexible shell,
    an inlet tube having a first end in communication with fluid and a second end received in the shell,
    a one-way directional flow device housed within said shell and in communication with the second end of the inlet tube,
    said one-way directional flow device having a pair of overlying membranes in tension which provide a slit-like opening, said membranes being held in tension by plates,
    a fluid chamber reservoir within said shell said reservoir serving to collect fluid exiting the one-way directional flow device through the slit-like opening,
    an outlet tube in communication the shell.

16. The medical device of claim 15 where the shell is compressed when external pressure is applied to said shell.

17. The medical device of claims 16 where the shell resists compression when said outlet tube is blocked.

18. The medical device of claims 16 where said shell remains compressed when said inlet tube is blocked.

19. A method for treating hydrocephalus by draining the fluid from the cranial vault of a patient, including the steps of
    (a) providing a medical device, including
        a valve having a membrane held in tension by plates and including a slit-like opening, said membrane having an aperture therein,
        a flexible shell which encloses the valve, said shell having a reservoir and first and second ends, with said first and second ends having openings therein,
        an inlet tube in communication with the valve through the aperture, said inlet tube having an end portion received by the opening at the first end of the shell, and a free end adapted to be inserted into the cranial vault, and
        an outlet tube in communication with the reservoir, said outlet tube having one end portion received by the opening at the second end of the shell, and a free end adapted to be insert into the patient's body,
    (b) attaching the medical device to the patient with the flexible shell facing outward,
    (c) inserting the free end of inlet tube into the cranial vault to enable fluid to drain through the free end of the inlet tube into the reservoir in the medical device,
    (d) inserting the free end of the outlet tube into the patient's body to enable fluid to drain from the reservoir into the body of the patient.

20. The method of claim 19 where the valve includes a pair of plates holding the membrane in tension, with the membrane forming a chamber and the slit-like opening closing and opening in response to the internal pressure within the chamber, said pressure with the chamber increasing and decreasing as the intracranial pressure varies.

21. The method of claim 20 where the shell is compressed when external pressure is applied to said shell.

22. The method of claims 21 where the shell resists compression when said outlet tube is blocked.

23. The method of claims 21 where said shell remains compressed when said inlet tube is blocked.

24. A process for making a medical device including the steps of:

(a) providing a top cover member and a base plate member which upon being connected form a flexible shell, (b) providing a one-way directional flow device disposed between the top cover member and the base plate member prior to forming the shell, said one-way directional flow device including a membrane held in tension by plates and including a slit-like opening, (c) connecting the top cover member and the base plate member to enclosed the one-way directional flow device within the shell, (d) providing an inlet tube and an outlet tube, and connecting the inlet tube to the one-way directional flow device and connecting the outlet tube to the shell.

25. A process for making a medical device including the steps of:

(a) providing a base plate, a top plate, an inlet tube, an outlet tube, and a flexible membrane with an opening and at least a pair of holes adapted to be aligned upon folding the membrane, (b) positioning and affixing the inlet tube to the opening, (c) folding the membrane to align at least some of the holes, d) placing the membrane between the base plate and the top plate, one of said plates having pins extending outward, (e) inserting the pins through the aligned holes, (f) ultrasonically welding the pins in place, (g) injection molding a first part and a second part of a shell, said parts of the shell being made of a flexible material with the first part having a raised portion, (h) positioning the assembly of the folded membrane, attached inlet tube, and the base and top plates between the first and second parts of the shell and assembling said first and second parts to form an internal reservoir, said shell having first and second openings, first opening adapted to receive the inlet tube and the second opening adapted the outlet tube, (i) affixing the inlet and outlet tubes to the shell.

* * * * *